United States Patent [19]

Perrin

[11] Patent Number: 5,478,841

[45] Date of Patent: * Dec. 26, 1995

[54] FLUORINATED QUINOLONES, PROCESS FOR THEIR PREPARATION AND PHARMACEUTICAL PREPARATIONS CONTAINING SAME

[75] Inventor: Claude Perrin, Orsay, France

[73] Assignee: Bouchara S.A., Levallois Perret, France

[ * ] Notice: The portion of the term of this patent subsequent to Jul. 26, 2011, has been disclaimed.

[21] Appl. No.: 185,918

[22] PCT Filed: May 25, 1993

[86] PCT No.: PCT/FR91/00505

§ 371 Date: Feb. 7, 1994

§ 102(e) Date: Feb. 7, 1994

[87] PCT Pub. No.: WO93/24479

PCT Pub. Date: Dec. 9, 1993

[30] Foreign Application Priority Data

May 26, 1992 [FR] France ................... 92 06404

[51] Int. Cl.$^6$ ................ C07D 215/233; C07D 215/38; A61K 31/475
[52] U.S. Cl. ........................... 514/312; 546/156
[58] Field of Search ............... 546/156; 514/312

[56] References Cited

U.S. PATENT DOCUMENTS

| | | | |
|---|---|---|---|
| 4,282,212 | 8/1981 | Berger | 544/111 |
| 4,657,913 | 4/1987 | Mich | 546/156 |
| 4,753,953 | 6/1988 | Masuzawa | 514/312 |
| 4,851,418 | 7/1989 | Sanchey | 514/300 |
| 4,894,458 | 1/1990 | Masuzawa | 546/156 |
| 4,927,926 | 5/1990 | Corominas | 544/101 |
| 4,997,943 | 3/1991 | Iwata | 544/363 |
| 5,043,450 | 8/1991 | Masuzawa | 546/156 |
| 5,045,549 | 9/1991 | Sauter | 514/312 |
| 5,047,538 | 9/1991 | Domagala | 546/156 |
| 5,051,509 | 9/1991 | Nagano | 546/156 |
| 5,061,712 | 10/1991 | Petersen | 514/300 |
| 5,073,556 | 12/1991 | Iwata | 514/254 |
| 5,097,032 | 3/1992 | Domagala | 546/156 |
| 5,116,834 | 5/1992 | Domagala | 514/212 |
| 5,284,842 | 2/1994 | Petersen | 514/187 |
| 5,324,837 | 6/1994 | Renga | 544/333 |
| 5,328,908 | 7/1994 | Demuth | 514/254 |
| 5,332,749 | 7/1994 | Perrin | 514/312 |
| 5,342,844 | 8/1994 | Laborde | 514/300 |
| 5,342,846 | 8/1994 | Singh | 514/312 |

OTHER PUBLICATIONS

J. S. Kieley, "Quinolone Antibacterials ...", J. Med. Chem., vol. 34(2), pp. 656–663, Feb. 1991.

J. M. Domagala, "New Structures–Activity Relationships ...", J. Med. Chem., vol. 29(3), pp. 394–404, Mar. 1986.

D. T. W. Chu, "Synthesis end Structures–Activity ...", J. Med. Chem., vol. 28(11), pp. 1558–1564, Nov. 1985.

*Primary Examiner*—Bernard Dentz
*Assistant Examiner*—D. Margaret M. Mach
*Attorney, Agent, or Firm*—Bierman and Muserlian

[57] ABSTRACT

Antibacterial compounds of the following formula

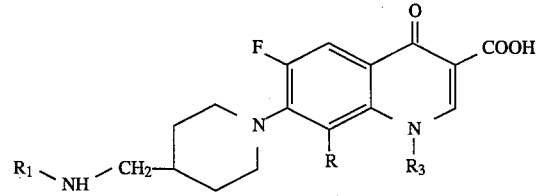

where the variables are as in claim 1 and their pharmaceutically acceptable bases.

3 Claims, No Drawings

FLUORINATED QUINOLONES, PROCESS FOR THEIR PREPARATION AND PHARMACEUTICAL PREPARATIONS CONTAINING SAME

This application is a 371 of PCT/FR 93/00505, filed 25 May 1995.

A subject of the present invention is new quinolones and more particularly quinolones substituted by a piperidine ring.

More particularly a subject of the invention is new piperidinyl quinolone 3-carboxylic acids endowed with useful antibacterial properties.

Specifically a subject of the invention is new 6-fluoro-7-piperidine-quinolone-3-carboxylic acids of general formula I:

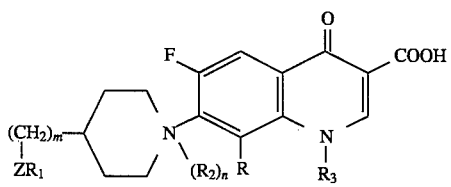

in which

R is hydrogen or fluorine

Z is an amino radical $R_1$ represents hydrogen, an (optionally hydroxylated lower alkyl) radical, an acyl radical derived from an organic carboxylic acid, an alkyl carbonic acid or an aryl sulphonic acid or an arylamino carbonyl radical of form:

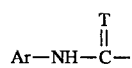

in which

Ar represents a mono- or bicyclic aromatic radical optionally substituted by one, two or three substituents chosen from lower alkyls, halogens and trifluoromethyl T represents oxygen or sulphur m is equal to 1

X represents hydrogen or fluorine

Y represents hydrogen or fluorine and $R_3$ is chosen from the group constituted by an isopropyl radical, a tertbutyl radical, a cyclopropyl radical, a (cyclopropyl) alkyl radical, a phenyl radical or a phenyl radical substituted by one, two or three substituents defined previously $R_2$ represents an oxygen atom linked by a semi-polar bond and n is equal to 0 or 1.

Among the compounds of the invention five sub-groups are distinguished:

the amino derivatives of formula $I_A$:

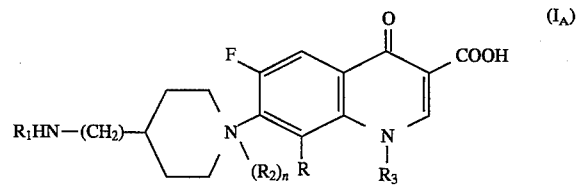

in which $R_1$ represents hydrogen, a linear or branched lower alkyl radical optionally substituted by a hydroxyl or an acyl radical defined as above R, $R_2$ and n are defined as previously and $R_3$ is a cyclopropyl radical the amino derivatives of formula $I_B$

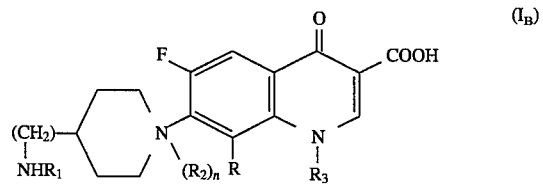

in which $R_1$ represents hydrogen, a linear or branched lower alkyl radical optionally substituted by a hydroxyl or an acyl radical derived from a carboxylic, carbonic or arylsulphonic acid $R_3$ is a tertbutyl radical and the substituents R, $R_2$ and n are defined as previously the amino derivatives of formula $I_C$

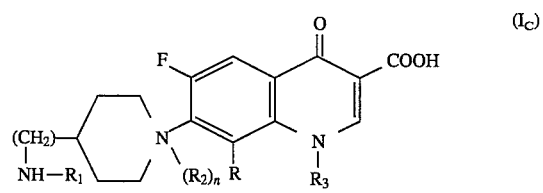

in which $R_3$ represents an isopropyl radical and the substituents R, $R_1$, $R_2$ and n have the meanings provided previously the amino derivatives of formula $I_D$

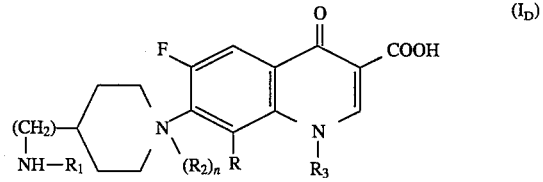

in which $R_3$ represents a phenyl radical optionally substituted by one, two or three substituents and the substituents $R_1$, $R_2$, R and n have the meanings provided previously and the amino derivatives of formula $I_E$

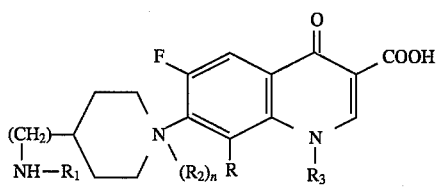

in which

R$_3$ represents a (cyclopropyl) alkyl radical in which the alkyl remainder a has 1 to 3 carbon atoms and the substituents R$_1$, R$_2$, R and n have the meanings provided previously.

Among the compounds of general formula (I), the compounds in which ZR$_1$ is an ureido function are those which are currently preferred.

Particular emphasis is also given to the ureidic compounds of formula I$_F$:

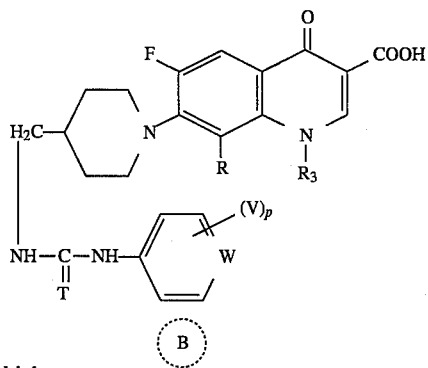

in which

R and R$_3$ have the meanings provided previously

T represents oxygen or sulphur

W is a group $\geq$C—H or $\geq$N

B is hydrogen or an aromatic structure with 5 or 6 members

V is hydrogen, a lower alkyl radical, a trifluoromethyl radical or a halogen and p is equal to 1, 2 or 3.

Among the compounds of general formula I, the compounds in which ZR$_1$ is an ureido function are those which are currently preferred.

The compounds according to the invention can be salified by the addition of a mineral or organic base. The main salts which can be used are those of alkali metals, alkaline-earth metals, ammonium, iron, aluminium, alkylamine salts, hydroxylalkylamine salts, phenylalkylamine salts, pyridylalkylamine salts, cyclanylamine salts, dicyclanylalkylamine salts . . .

Among the salts, sodium, lithium, ammonium, N-methylglucamine and tromethanol salts are those which are currently preferred.

These compounds can also be salified by a strong mineral or organic acid when R$_1$ represents hydrogen, a lower alkyl radical or a lower (hydroxyalkyl) radical. Among these, the hydrochlorides, methanesulphonates, lactates or acetates are preferred examples.

Among the compounds of general formula I, there can be mentioned quite particularly:

6,8-difluoro 1-cyclopropyl-7-((4-aminomethyl)-1-piperidinyl)-quinolone-3-carboxylic acid and its addition salts with a mineral or organic acid 6-fluoro-1-cyclopropyl-7-((4-aminomethyl)-1-piperidinyl)-quinolone-3-carboxylic acid and its addition salts with a mineral or organic acid.

The compounds according to the invention possess remarkable antibacterial properties, in particular against Gram positive bacteria.

Moreover, they possess the property of being moderately resorbed by general route in such a way that their elimination is essentially faecal.

Therefore they can be used effectively as medicaments for bacterial infections of the alimentary canal, for the treatment of bacterial dysenteries, of traveller's diarrhoea or of intestinal infections. They can also be used by topical route for the treatment of ocular infections or infections of the acoustic duct.

To this end, the compounds according to the invention will be used in the form of pharmaceutical compositions in which the active ingredient of general formula I or one of its salts, is added to or mixed with a pharmaceutically acceptable, non-toxic, inert excipient or vehicle.

The most appropriate pharmaceutical forms are those intended for administration by digestive route such as solutes or drinkable suspensions, granules, capsules, uncoated or coated tablets, sugar-coated pills, sachets of powder, flavoured or not, sweetened or not, pills or cachets.

Solutions, creams, lotions, salts for topical application can also be used as an external antibacterial agent.

The average dose depends principally on the severity of the infection and of the sensitivity of the microbial germ to the antibacterial agent. The unit dose ranges from 100 to 600 mg per dose. The daily dose ranges form 200 to 1200 mg spread over 2 to 4 doses.

The invention also relates to a process for obtaining the compounds of general formula I which consists of reacting a 6-fluoro-7-halogeno-1-R$_3$-4-oxo-1,4-dihydroquinoline-3-carboxylic acid of formula II:

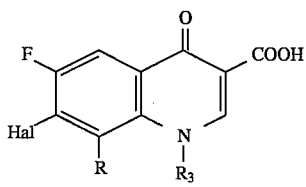

in which

Hal represents an easily-exchangeable halogen atom and the substituents R and R$_3$ have the meanings provided previously with 4-aminomethyl piperidine of formula III:

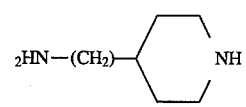

in order to form a 6-fluoro-1-R$_3$-7-((4-aminomethyl)-1-piperidinyl)-4-oxo-1,4-dihydroquinoline-3-carboxylic acid of formula IV:

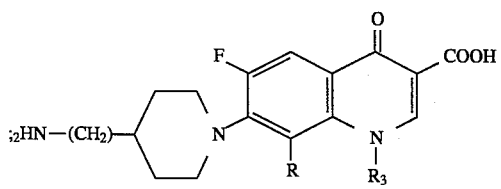

in which

R$_3$ and R have the meanings provided previously which, if desired, can be salified by the addition of a mineral or organic base converted into the addition salt by the addition of a mineral or organic acid N-oxidized by the action of a mineral or organic hydroperoxide alkylated by the action of an alkyl halide in basic medium or acylated by reacting with a functional derivative of carboxylic or sulphonic acid or also with an alkyl halogenoformate.

The invention also relates to a process for converting the amino compound of formula IV into urea or thiourea which consists of subjecting the compound of formula IV to the action of an isocyanate or isothiocynanate of formula:

Ar—N=C=T in which

Ar and T have the definitions provided previously in solution in an inert solvent, in order to obtain the ureidic derivative of formula V:

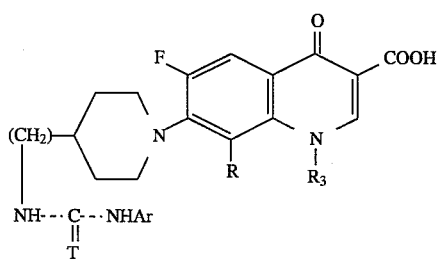

in which

R, R$_3$, T and Ar are defined as previously.

The following examples illustrate the invention without however limiting it.

EXAMPLE X 6,8-difluoro-7-[(4-aminomethyl)-1-piperdinyl]-1-(1-cyclopropyl)-4-oxo-1,4-dihydroquinolinyl-3-carboxylic acid (Compound 1)

A solution of 3 g (0.02M) of 6,8-difluoro-7-chloro-1-cyclopropyl-4-oxo-1,4-dihydroquinoline-3-carboxylic acid and 3.6 g (0.03M) of 4-aminomethyl-piperidine in 30 ml of pyridine is heated under reflux for 5 hours.

At the end of this period of heating the crystals formed are taken up in 50 cm$^3$ of ethanol and the precipitate is separated out.

The precipitate is suspended in 50 cm$^3$ of water for 30 minutes then separated, washed with water, washed with ethanol and dried. In this way 2 g of crystals are collected melting (on a Koffler block) above 260° C. (the yield is 50% of the theoretical). The IR spectrum and the microanalysis are in accordance with an anhydrous product. The hydrochloride formed by taking up with 1N hydrochloric acid (30 cm$^3$) also melts above 260° C. (yield 76%). The hydrochloride is in the form of pale yellow crystals which are moderately soluble in water.

The following were prepared in the same way:

6-fluoro-1-cyclopropyl-7-((4-aminomethyl)-1-piperidinyl)-quinolone-3-carboxylic acid (compound 5)—(M.P.=236° C.) with a yield of 75%

The hydrochloride obtained with a yield of 55% melts above 260° C.

6,8-difluoro-1-(2,4-difluorophenyl)-7-((4-aminomethyl)-1-piperidinyl)-quinolone-3-carboxylic acid—(M.p.>260° C.) with a yield of 48%

The hydrochloride obtained with a yield of 55% melts at 250° C.

6,8-difluoro-1-(cyclopropylmethyl)-7-((4-aminomethyl)-1-piperidinyl)-quinolone-3-carboxylic acid—(M.p.=265° C.) with a yield of 72%

The hydrochloride obtained with a yield of 85% melts above 260° C.

6-fluoro-1-tertbutyl-7-((4-aminomethyl)-1-piperidinyl)-quinolone-3-carboxylic acid—(M.p.>260° C.) with a yield of 24%

The hydrochloride obtained with a yield of 66% melts above 260° C.

6,8-difluoro-1-isopropyl-7-((4-aminomethyl)-1-piperidinyl)-quinolone-3-carboxylic acid (compound 7)—(M.p.=250° C.) with a yield of 88%

The hydrochloride obtained with a yield of 85% melts above 260° C.

The other 7-((4-aminomethyl)-piperidinyl)-quinolonecarboxylic acids are prepared by the action of 4-aminomethyl piperidine on the corresponding 7-fluoro quinolone carboxylic acids.

They are isolated and tested in the form of hydrochloride or methane sulphonate.

EXAMPLE II

Bacteriological study of the compounds according to the invention

Material and Methods

The products were tested vis-à-vis 7 reference strains
* 4 gram positive genera:
  *Bacillus subtilis* ATCC 9372
  *Straphylococcus aureus* ATCC 25923
  *Streptococcus faecalis* ATCC 8043
  *Staphylococcus aureus* CB 951
* 3 gram negative genera:
  *Escherichia coli* ATCC 25922
  *Pseudomonas aeruginosa* ATCC 22853
  *Acinetobacter calcoaceticus* variety anitratum ATCC 17903

(*= microplates and inoculator from Dynatech)

Measurement of the minimal inhibitory concentrations was carried out by a microdilution technique (*) in liquid medium (Mueller-Hinton broth) in a volume of 100 µl and for a range of concentrations varying from 128 to 0.6 mg/liter, prepared from a mother solution of antibiotic titrating 512 mg/liter. The preparation of these mother solutions produced, varied according to the molecules as a function of solubility criteria.

The inoculation is carried out by adding to each cupule 10 µl of a dilution in physiological water of an 18 hour broth of heart/brain broth such that each cupule contains about 10$^6$ bacteria/ml.

The minimal inhibitory concentration is read as the first concentration of antibiotic giving no culture which is macroscopically visible after incubation for 18 hours at 37° C.

EXAMPLE III

Tablets of 7-((4-aminomethyl)-1-piperidinyl)-6,8-difluoro-1-ethyl-4-oxo-1,4-dihydroquinolinyl-3-carboxylic acid hydrochloride at 250 mg

| | |
|---|---|
| 7-((4-aminomethyl)-1-piperidinyl)-6,8-difluoro-1-cyclopropyl-4-oxo-1,4-dihydroquinolinyl-3-carboxylic acid hydrochloride | 250 g |
| Maize starch | 40 g |
| Wheat starch | 40 g |
| Carboxymethyl starch | 20 g |
| Polyvidone excipient | 10 g |
| Microcrystalline cellulose | 30 g |
| Magnesium stearate | 10 g | for 1,000 finished tablets with an average weight of 0.400 g.

EXAMPLE IV

Opthalmic drops based on 7-((4-aminomethyl)-1-piperidinyl)-6,8-difluoro-1-cyclopropyl-4-oxo-1,4-dihydroquinolinyl-3-carboxylic acid lactate

| | |
|---|---|
| 7-((4-aminomethyl)-1-piperidinyl)-6,8-difluoro-1-cyclopropyl-4-oxo-1,4-dihydroquinolinyl-3-carboxylic acid lactate | 3 g |
| Disodium tetracemate | 0.1 g |
| Disodium phosphate | 0.05 g |
| Monosodium phosphate | 0.04 g |
| Sodium hypophosphite | 0.02 g |
| Methylparaben | 0.015 g |
| Distilled water s.q.f. | 100 ml |

One drop contains 0.005 g of active ingredient.

I claim:

1. A compound selected from the group consisting of a compound of the formula

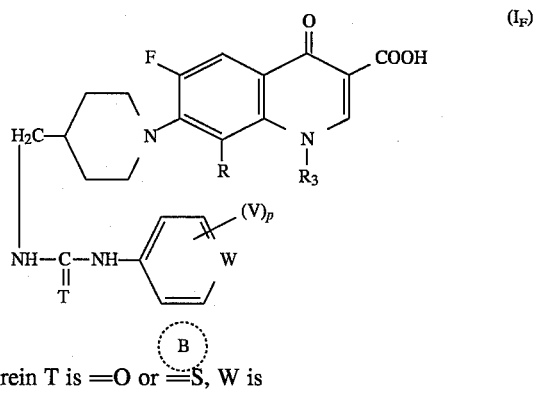

wherein T is $=O$ or $=S$, W is

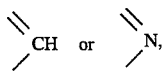

B is hydrogen or an aromatic of 5 to 6 ring members, V is selected from the group consisting of hydrogen, lower alkyl, $-CF_3$ and halogen, p is an integer from 1 to 3, R is hydrogen or fluorine, $R_3$ is selected from the group consisting of cyclopropyl and phenyl optionally substituted with 1 to 3 members of the group consisting of lower alkyl, $-CF_3$ and halogen or its salts with a non-toxic pharmaceutically acceptable base.

2. An antibacterial composition comprising a bactericidally effective amount of a compound of claim 1.

3. A method of combatting bacterial infections in warm-blooded animals comprising administering to warm-blooded animals a bactericidally effective amount of a compound of claim 1.

TABLE

MINIMAL INHIBITORY CONCENTRATION (MIC) AND MINIMAL BACTERICIDAL CONCENTRATION (MBC) (in µg/ml)

| Bacterial Genus / Product | S. aureus ATCC 25923 | | S. faecalis ATCC 25922 | | E. coli ATCC 25922 | | P. aeruginosa ATCC 22853 | | Acinetobacter Baumanii ATCC 17904 | | S. aureus CB-951 (1) | |
|---|---|---|---|---|---|---|---|---|---|---|---|---|
| | MIC | MBC | MIC | MBC | MIC | MBC | MIC | MBC | MIC | MBC | MIC | MBC |
| Compound 1 | 0.06 | 0.06 | 1 | 1 | 2 | 4 | >16 | >16 | 0.03 | 0.03 | 0.25 | 0.25 |
| Compound 2 | 0.015 | 0.015 | 0.25 | 0.5 | 2 | 2 | >16 | >16 | 0.003 | 0.007 | 0.03 | 0.06 |
| Compound 3 | >51.2 | >51.2 | >51.2 | >51.2 | >51.2 | >51.2 | >51.2 | >51.2 | | | >51.2 | >51.2 |
| Compound 4 | 0.06 | 0.12 | 0.12 | 0.12 | 0.06 | 0.06 | 1 | 1 | 0.12 | 0.12 | 2 | 2 |
| Compound 5 | 0.25 | 0.5 | | | 0.25 | 0.5 | | | | | | |
| Compound 6 | 1.6 | 3.2 | 1.6 | 12.8 | 0.4 | 0.4 | 12.8 | >51.2 | | | | |
| Compound 7 | 3.2 | 6.4 | 3.2 | 25.6 | 1.6 | 1.6 | 25.6 | >51.2 | | | | |
| Cyprofloxacine | 0.25 | 0.25 | 0.25 | 0.25 | 0.007 | 0.007 | 0.12 | 0.21 | 0.06 | 0.06 | 4 | 4 |
| Pefloxacine | 0.12 | 0.25 | 1 | 1 | 0.06 | 0.06 | 2 | 2 | 0.06 | 0.06 | 4 | 4 |

(1) *Staphylococcus methicillino* - resistant *pefloxacino* - resistant

* * * * *